(12) United States Patent
Kemperman et al.

(10) Patent No.: US 7,994,314 B2
(45) Date of Patent: Aug. 9, 2011

(54) METHOD FOR THE PREPARATION OF AN ENANTIOMERICALLY PURE BENZAZEPINE

(75) Inventors: Gerardus Johannes Kemperman, Oss (NL); Johannes Paulus Gerardus Seerden, Groningen (NL)

(73) Assignee: N.V. Organon, Oss (NL)

( * ) Notice: Subject to any disclaimer, the term of this patent is extended or adjusted under 35 U.S.C. 154(b) by 289 days.

(21) Appl. No.: 12/098,677

(22) Filed: Apr. 7, 2008

(65) Prior Publication Data

US 2008/0255349 A1 Oct. 16, 2008

Related U.S. Application Data

(60) Provisional application No. 60/922,831, filed on Apr. 11, 2007.

(51) Int. Cl.
*C07D 471/14* (2006.01)

(52) U.S. Cl. ........................................ 540/577; 540/578

(58) Field of Classification Search .................. 540/578, 540/577

See application file for complete search history.

(56) References Cited

U.S. PATENT DOCUMENTS 4,062,848 A 12/1977 van der Burg

FOREIGN PATENT DOCUMENTS

| GB | 1567997 | 5/1980 |
|----|---------|--------|
| WO | WO2005/005410 | 1/2005 |
| WO | WO00/62782 | 10/2010 |

OTHER PUBLICATIONS

Che, et al., "Synthesis of novel tricyclic pyrimidine-fused 5,6-dihydrobenzodiazepines via a Pictet-Spengler-like cyclizatin", Tetrahedron, vol. 62, pp. 2563-2568, (2006).

Matsuo, et al., "Synthesis of the Novel Furo [3,4-*b*][1,5]benzodiazepinone and Pyrrolo [3,4-*b*][1,5]benzoldiazepinone Systems", Chem. Phar. Bull. vol. 32, No. 9, pp. 3724-3729 (1984).

Singal, et al., "A novel one pot photochemical sysnthesis of substituted 2-oxo-1,2,21,11-tetrahydro-benzo [3,4-a] imidazolo [3,4-a] quinolines", Synthetic Communications, vol. 15, No. 9, pp. 829-836 (1985).

Wynia, et al., "Development and validation of a capillary electrophoresis method within a pharmaceutical quality control environment and comparison with high-performance liquid chromatography", Journal of Chromatography A., vol. 773, No. 1-2, pp. 339-350 (1997).

Yanai, et al., "Convenient synthesis of fluorinated quinoline, 1,2-dihydroquinoline, and 1,2,3,4-tetrahydroquinoline derivatives", Tetrahedron, vol. 63, No. 10, pp. 2153-2160 (2007).

European Search Report for European Patent Application No. 07105979.4-1521 mailed date Jan. 17, 2008.

An International Search Report and Written Opinion, dated Sep. 9, 2008, which issued during the prosecution of International Application No. PCT/EP2008/054315, which corresponds to the present application.

*Primary Examiner* — Bruck Kifle

(74) *Attorney, Agent, or Firm* — Susan L. Hess; Gerard M. Devlin

(57) ABSTRACT

The invention relates to the preparation of mirtazapine precursors and mirtazapine preferably having a substantial enantiomeric excess.

10 Claims, No Drawings

METHOD FOR THE PREPARATION OF AN ENANTIOMERICALLY PURE BENZAZEPINE

This application claims priority based on U.S. Provisional Patent Application No. 60/922,831, filed Apr. 11, 2007.

The invention relates to a method for the preparation of an enantiomerically pure benzazepine, in particular of mirtazapine, in substantial enantiomeric excess of the R or S form. The invention further relates to novel intermediates and their use for the preparation of mirtazapine having a substantial enantiomeric excess of the R or S form.

Mirtazapine (1,2,3,4,10,14b-hexahydro-2-methylpyrazino[2,1-a]pyrido[2,3c][2]benzazepine) is a tetracyclic compound having the formula A:

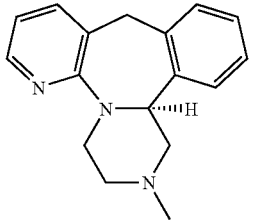

Formula A

The compound is chiral and the racemic mixture finds widespread use as a medicine for the treatment of depression. Other medical uses for mirtazapine have also been reported e.g., WO 99/25356 and WO 01/58453 disclose its use in the treatment of sleep disorders and apnea. Investigations into the biological effects of the enantiomers of mirtazapine (e.g. O'Connor and Leonard, Neuro-pharmacology, 1986, vol. 25, pp. 267-270; Kooyman et al., 1994, vol. 33, pp. 501-507; De Boer et. al., Neuro-pharmacology, 1988, vol. 27, pp. 399-408; Gower et al., 1988, vol. 291, pp 185-201) mention properties of the compound in its pure enantiomeric forms. The present invention provides for an efficient production of large quantities of enantiomerically pure mirtazapine and related benzazepines.

The term "enantiomerically pure", "optically pure" and "having a substantial enantiomeric excess" are used interchangeably and all imply a mixture of R and S enantiomers comprising a substantial enantiomeric excess of the R or S enantiomer. In the context of the present invention a substantial enantiomeric excess preferably is an enantiomeric excess of at least 80%.

A variety of methods are known in the art for the preparation of mirtazapine in racemic or enantiopure form. According to the method described in U.S. Pat. No. 4,062,848 mirtazapine can be obtained as a result of ring closure of a compound of Formula B using a variety of dehydrohalogenating agents.

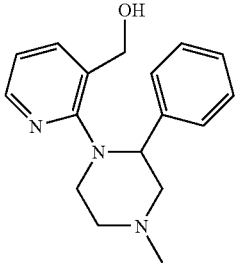

Formula B

Examples of such agents include acids such as sulphuric acid, concentrated hydrochloric acid, picric acid, trifluoroacetic acid, phosphoric acid, polyphosphoric acid (PPA), phosphorus oxychloride, phosphorus trioxide, phosphorus pentoxide and Lewis Acids such as aluminium chloride, ferric chloride, zinc chloride, tin chloride, titanium chloride, boron trifluoride, antimony pentachloride and zirconium tetrachloride. In U.S. Pat. No. 4,062,848 preparation of mirtazapine is exemplified by ring closure using concentrated sulphuric acid. In WO00/62782 it is indicated that concentrated sulphuric acid is most preferred. The optical resolution of racemic mirtazapine has also been addressed in U.S. Pat. No. 4,062,848. By the method disclosed in U.S. Pat. No. 4,062,848, enantiomerically pure mirtazapine is obtained by forming diastereomeric salts by reaction of racemic mirtazapine with enantiomerically pure dibenzoyltartaric acid in ethanol, filtering off the thus formed diastereomeric salt, followed by regeneration of the free base by treatment with aqueous ammonia.

In document WO 2005/005410 is described that for the synthesis of enantiomerically pure mirtazapine by ring closure of an enantiomerically pure compound of above formula (A), stereochemical integrity in the starting material can be preserved by making a specific selection out of the above mentioned ring closing reagents. The method comprises a step of ring closure of a compound according to formula (A), said step comprising treatment, wherein mirtazapine with enantiomeric excess is formed by the ring closure of the compound of formula (A) with enantiomeric excess by treatment with a suitable acid in the absence of a solvent or a suitable combination of an acid and an organic solvent. The inventors have found that the reaction described in WO 2005/005410 can proceed without substantial racemisation by selection of the appropriate conditions, but that under such conditions a significant amount of side products is formed that complicates purification of the enantiopure mirtazapine and consequently diminishes the overall yield of the process Reversely, preparation conditions that aim to reduce the amount of side products again proceed with substantial racemisation.

In the described prior ad methods resolution occurs at the end of the synthetic pathway leading to the generation of a racemic mixture of mirtazapine. It follows therefore that the overall yield of each enantiomerically pure compound obtained is relatively low and can never be more than 50%. It would be beneficial to have a more economic method in which mirtazapine with substantial enantiomeric excess could be prepared with an overall improved yield. In U.S. Pat. No. 4,062,848 a general remark is made that pure enantiomers of mirtazapine may also be prepared directly by starting from optically active precursors. However, it is not described how to obtain such precursors in enantiomeric excess or how to retain the enantiomeric excess throughout the subsequent reaction steps for the manufacture of mirtazapine. The methods described in U.S. Pat. No. 4,062,848 and WO00/62782 with concentrated sulphuric acid do not sufficiently retain the enantiomeric excess. The skilled man still has the problem of choosing between a low yield or, when using optically pure precursors, a low enantiomeric excess.

It is a general object of the invention to provide an alternative method for the preparation of mirtazapine having substantial enantiomeric excess and which has a higher overall yield and can therefore be less expensive. It is a further object of the invention to provide intermediates for the preparation of mirtazapine that can be used in a process for the preparation of mirtazapine without substantial racemisation or side products formation and preferably can also easily be obtained in enantiomerically pure form.

According to the invention there is provided a method for the preparation of a cyclic compound according to formula III comprising reacting a compound according to Formula I and a compound according to formula II,

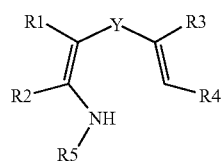

Formula I

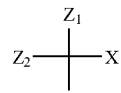

Formula II

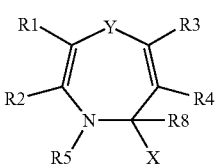

Formula III wherein in Formula I, $R_1$, $R_2$, $R_3$ and $R_4$ may be hydrogen or substituent groups comprising one or more carbon atoms and/or heteroatoms, wherein $R_1$, $R_2$, $R_3$ and $R_4$ can be combined in aromatic or aliphatic ring structures.

Y is a ring element comprising 1-3 substituted or unsubstituted carbon atoms and/or heteroatoms in the ring and $R_5$ is hydrogen or a hydrocarbon substituent group comprising one or more carbon atoms and optionally one or more hetero atoms, and wherein in Formula II, $Z_1$ and $Z_2$ are, leaving groups, X is a reactive functional hydrocarbon group for subsequent ring closure, comprising one or more carbon atoms and a reactive functional group and having a chain of between 1 to 6 atoms between the carbon atom attached to the central carbon atom of formula II and the reactive functional group and $R_6$ is hydrogen or a hydrocarbon substituent different from X making the central carbon atom of formula it a chiral centre in Formula III.

The compound according to formula I comprises a primary or secondary amine connected via 2 carbon atoms having an unsaturated bond, ring element Y and again to carbon atoms having an unsaturated bond to a reactive hydrogen atom. Said hydrogen atom is reactive because it is connected to an unsaturated bond. It is believed that the unsaturated bond adjacent to the amine group stereochemically facilitates the reaction between the amine and said reactive hydrogen atom. The ring element Y can optionally be combined with other substituent groups $R_1$, $R_2$, $R_3$ and $R_4$ to form a cyclic structure.

In a preferred embodiment $R_3$ and $R_4$ are combined forming a substituted or unsubstituted aromatic ring, preferably a phenyl or pyridine ring it is considered that an aromatic ring promotes the reaction. The ring element Y may comprise 1, 2 or 3 ring atoms thus making the compound of formula III a seven, eight or nine membered ring. Preferably, Y is —O—, —$NR_9$— or —$CR_9R_{10}$— wherein $R_9$ and $R_{10}$ are hydrogen or hydrocarbon substituents that may be saturated or unsaturated and may optionally comprise hetero atoms.

The reaction between compound I and II is preferably carried out in the presence of a strong acid such as trifluoroacetic acid, methanesulfonic acid, toluenesulfonic acid, but most preferably sulphuric acid. The reaction between the compound of formula I and formula II proceeds by elimination of leaving groups $Z_1$ and $Z_2$ on compound II with the hydrogen on the amine and the reactive hydrogen. Although the substituents $R_1$, $R_2$, $R_3$ and $R_4$ are broadly defined, it is considered that preferably these substituents do not comprise primary or secondary amines or hydrogen atoms that are reactive with compound II. Suitable leaving groups $Z_1$ and $Z_2$ in formula II are each independently X hydroxy, alkoxy, chloride, bromide, iodide, triflate, mesylate, tosylate or besylate.

Good results were obtained in a method wherein the compound II represents a (hemi-)acetal (for R8=H) or (hemi-)ketal (for R8=hydrocarbon) according to formula IIa wherein $Z_1$ and $Z_2$ are $OR_6$ and $OR_7$ respectively wherein $R_6$ and $R_7$ are hydrocarbon or hydrogen, or the corresponding aldehyde (for R8=H) or ketone (for R8=hydrocarbon) according to formula IIb:

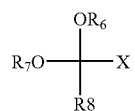

Formula IIa

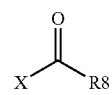

Formula IIb

Suitable example of compounds according to formula IIa or IIb are alkylaminoacetaldehyde dialkylacetals, halogen acetaldehyde dialkylacetal, alkyl-2,2-dialkoxyacetate, 2,2-dialkoxyacetal alkylamide, 2,2-dialkoxyacetal (2-hydroxy ethyl) alkyl amide.

The method according to the invention is very suitable for preparing compounds having multi-cyclic structures. Such compounds often have biologic activity and can be used for the preparation of pharmaceutical formulations. The group X in the context of the present invention is chosen in view of further cyclization reaction, in one or more reaction steps, between reactive functional group X and the nitrogen in the ring in formula III. However, it is noted that compound of formula III wherein Y=oxygen or sulphur are novel irrespective of the choice of group X, so in this compounds X may also be hydrogen or hydrocarbon that is not substituted with a reactive functional group.

Bioorg & Med. Chem. Let., 2002, 12, 3573-3577 describes a method for the preparation of benzazepine antagonist for the neurotransmitters serotonine (5-HT) involving a reaction between paraformaldehyde and a compound according to formula Ia. Similarly, Journal of Combinatorial Chemistry, 8(3), 381-387; 2006 describes a method to prepare a polycyclic structure by ring closure between an amine and an aromatic hydrogen atom using an ethylaldehyde. However, these methods do not disclose or teach to prepare an intermediate according to formula IIIa comprising a group X that can be extended to achieve a further ring closure, in particular it does not disclose or teach the preparation of mirtazapine or any of its precursors, more particular having a substantial enantiomeric excess.

In view of preparing polycyclic compounds, the compound of Formula I is preferably a bicyclic compound according to general Formula Ia for forming, according to the method of the invention, a tricyclic compound according to Formula IIIa, wherein I an II represent ring structures, preferably comprising between five and eight ring atoms optionally comprising a hetero atoms N, S or O. The ring structures I and/or II may comprise one or more substitute groups preferably selected from alkyl, aryl, alkyl-aryl or alkoxy optionally comprising one or more ethylenically unsaturated bonds and/or optionally comprising one or more hetero atoms, halogen, hydroxy or sulphur containing groups.

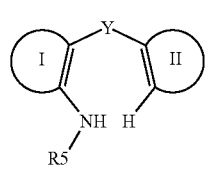

Formula Ia

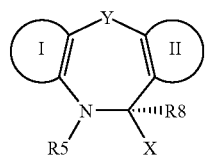

Formula IIIa

Most preferably, at least ring structure II, preferably both ring structure I and II represent a substituted or unsubstituted aromatic ring structure optionally comprising heteroatoms, preferably pyridine or phenyl, and wherein Y=O, N—R$_9$ or CR$_9$R$_{10}$ (R$_9$ and R$_{10}$ are hydrogen or substituents comprising saturated or unsaturated hydrocarbons optionally comprising hetero atoms). Most preferably ring II is a phenyl ring to form a benzazepine. Preferably, ring I is a phenyl or pyridine ring.

It is noted that all comments herein relating to generically described compounds similarly apply to the corresponding more specifically described compounds, for example comments to compounds of formulae I, II, III, IV and V similarly apply to compounds of formulae Ia, IIa, IIIa, IVa and comments to compounds IIIb apply to compounds IIIb1 and IIIb2 etc.

In a method for the preparation of mirtazapine, the compound according to Formula I is 2-amino-3-benzylpyridine of Formula Ib forming a novel mirtazapine precursor of formula IIIb. For the preparation of mirtazapine the group X is a reactive group comprising one or more carbon atoms and optional hetero-atoms chosen in view of one or more subsequent reaction steps to a following ring closure to form mirtazapine of Formula A.

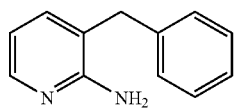

Formula Ib

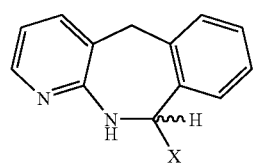

Formula IIIb

U.S. Pat. No. 4,062,848 describes a method for the preparation of tetracyclic compounds according to formula IIIa starting from tricyclic compounds according to formula Ia wherein Y is CH$_2$, R5 is H and ring II is a benzene ring. This method uses acid dihalogenide HalC(=O)(CH$_2$)$_n$Hal to get ring closure forming an imine ring which is subsequently reduced to a benzazepine according to Formula IIIa. This preparation route has several disadvantages compared to the method according to the invention. First of all, this preparation route cannot be used to prepare mirtazapine starting from the compound of Formula Ib because the acid di-halogenide will also react with the nitrogen of the pyridine. This document does indeed not describe the preparation of mirtazapine following this method. Further, this preparation route has the general disadvantage that the preparation of the benzazepine with formula III, IIIa, or IIIb involves 2 reaction steps whereas the method according to the invention only comprises one reaction step.

In a particularly preferred embodiment of the invention X is —C(=O)-Q, wherein Q is a substituent, preferably nitrogen, oxygen, or hydrogen or a substituent group comprising one or more carbon or hetero-atoms. The invention relates in particular to the mirtazapine precursor compound according to formula IIIb1 wherein X is —C(=O)-Q in racemic form, but more preferably in enantiomeric excess or enantiomeric pure R or S form.

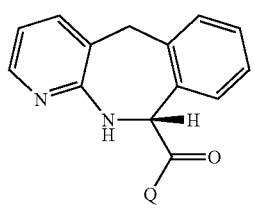

Formula IIIb1

The particular preference for this compound wherein X is —C(=O)-Q follows from its property that the chiral center adjacent to the ketone/carbonyl (>C=O) group can easily be racemised at elevated temperatures and/or mildly basic or acidic conditions and therefore can be used in a dynamic enantiomer resolution to obtain either of the enantiomers in theoretically hundred percent yield. Accordingly, a preferred method for the preparation of the compound of formula III wherein X is —C(=O)-Q in enantiomeric excess or enantiomeric pure form, comprises
1: subjecting a racemic mixture of said compound to an optical resolution step,
2: separating the desired enantiomer,
3: racemising the undesired enantiomer and
4: preferably recycling the racemised undesired enantiomer preferably to optical resolution step 1.

By racemising and recycling, the yield, defined as the amount in moles of the desired enantiomer divided by the amount in moles of the starting compounds of formula I or II is at least 70%, preferably at least 80%, more preferably at least 85%, more preferably at least 90% and most preferably at least 95%. The racemisation can be done preferably at slightly elevated temperatures under mildly basic or acidic conditions.

For the preparation of mirtazapine or other compounds of formula III having a methyl group adjacent to the chiral carbon, the method comprises a further step wherein the C=O group is reduced to a methylene group, in particular wherein X is —CH$_2$-Q is obtained by reduction of the compound wherein X is —C(=O)-Q (formula IX).

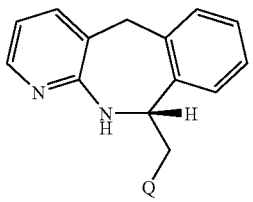

Formula IIIb2

It was found this can be done in an early stage or in any later stage during the preparation, preferably after ring closure where risk of racemization is less. In the method of the invention X can also be chosen to be —CH$_2$-Q, wherein Q is a substituent as defined above. In this method racemisation is not possible and optical resolution must be done using known methods, like diastereomer selective crystallisation. Although this inadvertently leads to a lower yield than the preparation route described above using the carbonyl precursor, it is still possible to obtain a good yield while producing considerably lower amounts of waste compared to prior art methods where the optical resolution step is done at a later stage in the preparation process.

The intermediate III is very useful for the preparation of optically pure mirtazapine and can be used for the preparation of S-mirtazapine, R-mirtazapine or for racemic mirtazapine. In principle all options presented can be applied for both enantiomerically pure or racemic mirtazapine. Esters (Q=OR in formula IIIb1) can be resolved by using a chiral acid such as (−)-dibenzoyl-L-tartaric acid yielding the (S)-enantiomer. The amide enantiomers (Q=NRH) can be resolved by using a chiral acid, for example enantiopure mandelic acid. A bromide precursor can be resolved via diastereoselective crystallization, for one sample with R(+)-mandelic acid giving the S-enantiomer. Similarly the opposite R-enantiomer can be obtained by resolution with S(−)-mandelic acid.

The group X in formula II is chosen in view of the subsequent reaction steps towards desired end products. In view of the general object to produce polycyclic structures, the intermediate compound according to formula IV can be prepared. Accordingly, in the preparation method a compound If is chosen wherein X is —C(=O)Q or —CH$_2$Q and wherein Q is chosen to be L(CHR)$_m$—(NR)$_p$—(CRH)$_n$— wherein each R may be the same or different substituent hydrogen or a hydrocarbon substituent comprising one or more carbon atoms and/or hetero atoms, p is 0 or 1, n is 0-2, m is 1-3 and m+n is 1-3 and L is a leaving group. For the formation of a six membered ring it is preferred that Q is -LC$_2$H$_4$NMe-, in order to obtain a precursor of formula IVa. In the preparation process for mirtazapine, said intermediate compound is the compound according to formula IVb.

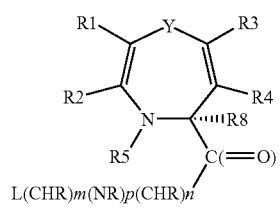

L(CHR)$m$(NR)$p$(CHR)$n$

Formula IV

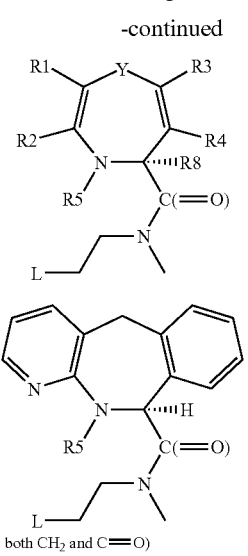

Formula IVa

Formula IVb (C(=O) implies both CH$_2$ and C=O)

Alternatively, instead of choosing a compound It that directly produces a compound of Formulae IV, IVa or IVb, a method can be followed wherein Q comprises a reactive group which is reacted with an extender according to the formula L(CHR)$_m$—(NR)$_p$—(CRH)$_n$A wherein A is a group reactive with Q For the preparation of compound of formula IVa or IVb (from compounds III, IIa, IIIb, IIIb1, or IIIb2, the group Q can be reacted with extension group -AC$_2$H$_4$L to form a group —NMeC$_2$H$_4$L. Good results were obtained in preparations wherein Q is a halogen, —NHR or —OR wherein R is a hydrogen or hydrocarbon substituent, preferably a C1-C4 alkyl. In case Q is a good leaving group, preferably halogen or —OR, A is RHN— or, reversely, in case Q is a RHN—group, A is a good leaving group, preferably halogenide or OR wherein R comprises a tolysate or mesylate. It was found for mirtazapine preparation that this extension reaction proceeds with a very high retention of optical purity. If the synthesis is started from an enantiopure form of compound III, the compound of formula IV can be obtained in enantiopure form.

A compound of formula IV wherein L is a weak leaving group can be converted into a compound according to formula V by modification of said weak leaving group L into a strong leaving group and subsequent ring closure in the presence of a base through nucleophilic displacement of the leaving group by the amidine in the ring. The strong leaving group L is preferably chosen from the group of chloride, bromide, iodide, methanesulfonate, toluenesulfonate, triflate, etc.

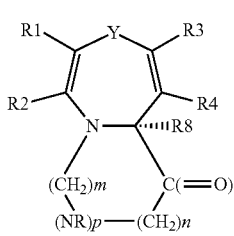

formula V

Leaving group L can be chosen to be a weak leaving group, preferably hydroxyl, to prevent interference with the reaction between Q and A. However, it is also possible in the extension reaction to directly proceed to ring closure forming the compound according to formula V in one step. In this case L in the compound of formula IV is chosen to be a stronger leaving group that can react directly with the amine in the presence of a base. In the method for the preparation of mirtazapine via compounds of Formula Ib, IIIb or IVb this results in mirtazapine according to formula A.

As described above, in case the compound is derived from an intermediate compound comprising a carbonyl group adjacent to the chiral center, a further reduction step can follow to reduce the carbonyl group >C=O to an ethylene group >CH$_2$.

The invention also relates to the intermediate compounds for the preparation of mirtazapine according to formulae IIIb, IVb or Vb in racemic, enantiomeric excess or enantiomeric pure R or S form and to any method for the preparation of mirtazapine in racemic, enantiomeric excess or enantiomeric pure R or S form using any of these compounds. U.S. Pat. No. 4,062,848 describes similar precursors only in generic terms, but not a preparation route specifically for the preparation of mirtazapine from such precursors. Mirtazapine precursor Ib indeed cannot be used because the acid di-halogenide will also react with the nitrogen of the pyridine ring resulting in an entirely different unwanted product.

Particularly preferred are intermediate compounds for the preparation of mirtazapine according to Formula IIIb1 in racemic form, in enantiomeric excess or enantiomeric pure R or S form, wherein Q is a reactive group for ring formation, preferably —NMeC$_2$H$_4$L halogen, —NHMe or —OR wherein R is hydrogen or a hydrocarbon substituent, preferably a C1-C4 alkyl. These components are preferred because they can easily be converted to a racemic state and recycled to the optical resolution step resulting in a very high yield.

Formula IIIb1

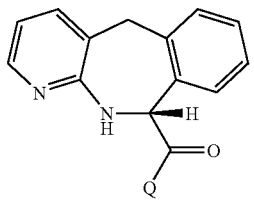

The invention also specifically relates to intermediate compounds for the preparation of mirtazapine according to Formula IIIb2 in enantiomeric excess or enantiomeric pure R or S form, wherein Q is a reactive group for ring formation, preferably —NMeC$_2$H$_4$L, halogen, —NHMe or —OR wherein R is hydrogen or a hydrocarbon substituent, preferably a C1-C4 alkyl.

Formula IIIb2

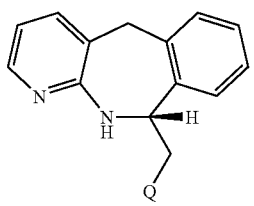

The invention also relates to precursor compounds in enantiomeric excess or enantiomeric pure R or S form according to general formula III, IV, and V. Although in the form, mentioned prior art document a broad statement is made that optically active compounds can be made from optically active precursors, it is considered that this broad statement does not provide a specific enabling pointer to enantiopure intermediate compounds. There is no disclosure of a specific optically active intermediate compound, no disclosure of a process to prepare such optically active compounds and no disclosure of a process using such optically active precursors. In fact all examples of enantiopure compounds were prepared only using an entirely different preparation route using entirely different precursors followed by optical resolution only of the end products. Further, inventors have found that a preparation method described in this prior art document results in considerable racemisation, so the broad statement is merely an unsubstantiated desideratum.

The invention further relates to compounds according to formula III or IIIa, wherein X is —C(=O)-Q or compounds according to formula IV, IVa, or V, comprising a C=O group adjacent to the chiral carbon atom and their use for the manufacture of the corresponding compounds having a substantial enantiomeric excess of the R or S enantiomer, optionally followed by reduction of the —C(=O)— group to a —CH$_2$— group. As described above these compounds having a C=O group adjacent to the chiral carbon can relatively easily be racemised allowing recycling of the racemised undesired enantiomer and a preparation process with a very high yield.

The invention will be illustrated by the following examples.

EXAMPLE 1

A methylamine compound according to formula IIIb2 wherein Q=NHMe (10,11-dihydro-5H-benzo[e]pyrido[2,3-b]azepin-10-ylmethyl)-methyl-amine) was prepared as described below using two different methods A and B.
Method A.

A mixture of 2-amino-3-benzylpyridine (2.1 g, 11.4 mmol) and N-methylaminoacetaldehyde dimethyl acetal (3.7 g, 31.1 mmol, 2.7 eq.) in a 250 ml round-bottomed flask was treated at room temperature with concentrated sulphuric acid (30 ml) by quick addition while stirring. A vigorous exothermic reaction took place. After stirring for 45 minutes the dark mixture was poured on ice water (250 ml). Concentrated ammonia (25% aq.; 150 ml) was added to basify the mixture. Extraction was done with ethyl acetate (3×150 ml). The combined organic layers were dried with Na$_2$SO$_4$. Evaporation under vacuum gave the crude 10,11-dihydro-5H-benzo[e]pyrido[2,3-b]azepin-10-ylmethyl)-methyl-amine as a yellow oil (2.5 g, 10.5 mmol) in 92% yield.

Mass analysis: M$^{+1}$=240 major peak.

$^1$H-NMR (CDCl$_3$) δ (ppm) 2.16 1H, br s, 1H; 2.54 3H, s, N—CH$_3$; 3.14-3.18 2H, m; 3.68 1H, d, J=15.2 Hz, CHH; 4.45 1H, d, J=15.2 Hz; 5.05 1H, dd, J=2.4 and 6.0 Hz; 5.55 1H, br s, NH; 6.49 1H, dd, J 5.1 and 7.5 Hz, ArH; 7.15 1H, m, ArH; 7.19-7.27 4H, m, ArH; 7.86 1H, dd, J=1.8 and 5.1 Hz, ArH.

Chiral HPLC analysis: column Chiralcel OJ (250×4.6 mm; 5 μm), mobile phase: n-heptane/EtOH/Et$_2$NH (90:10:0.2), flow: 1.0 ml/min, UV: 248 and 308 nm, sample: ~1 mg/ml in 2-propanol, injection: 10 μl, temp: 22° C. Enantiomers at 13.8 and 18.0 min. The product was used in subsequent steps without further purification.
Method B. Via Reduction of N-methylamide N-methylamide (700 mg, 2.77 mmol) was dissolved in THF (20 ml). The solution was cooled to 0° C. while stirring BF$_3$.OEt$_2$ (1.0 ml, 7.89 mmol, 2.8 eq.) was added and the mixture was stirred for 30 minutes at 0° C. Then BH$_3$.SMe$_2$ (3.0 ml, 2.0 M in THF; 6.0 mmol) was added. After stirring for 3 hours at room temperature the mixture was heated to reflux for 3 hours to give almost complete conversion. The mixture was then cooled to room temperature and 2N HCl was added to quench the excess borane, followed by the addition of water (20 ml) and ethyl acetate (100 ml). The organic layer was separated. The aqueous layer was extracted with dichloromethane (2×25 ml). The combined organic layers were dried with $Na_2SO_4$ and concentrated under vacuum to give an oil. Purification by chromatography on silica gel gave the pure product (298 mg, 1.25 mmol) in 45% yield.

Mass analysis: $M^{+1}$=240 major peak.

EXAMPLE 2

A bromine compound according to formula IIIb2 wherein Q=Br (10-bromomethyl-10,11-dihydro-5H-benzo[e]pyrido[2,3-b]azepine) was prepared as described below using two different methods A and B.

Method A. Neat

A mixture of 2-amino-3-benzylpyridine (12.0 g, 65.2 mmol) and bromoacetaldehyde dimethyl acetal (19 g, 112.4 mmol, 1.7 eq.) in a 250 ml round-bottomed flask was treated at room temperature with concentrated sulphuric acid (50 ml) by quick addition. A vigorous exothermic reaction took place. After stirring for one hour the dark mixture was poured on ice (ca. 500 ml). Concentrated ammonia was added to basify the mixture. Extraction was done with ethyl acetate (100 ml) and dichloromethane (2×150 ml). The combined organic layers were dried with $Na_2SO_4$. Evaporation under vacuum gave 10-bromomethyl-10,11-dihydro-5H-benzo[e]pyrido[2,3-b]azepine as a brown powder (14 g, 48.6 mmol) in 75% yield. Mass analysis: $M^{+1}$ 289,291 (Br-isotope) major peak.

$^1$H-NMR (CDCl$_3$) δ (ppm) 3.88 2H, d, J=6.9 Hz, CH$_2$Br; 3.95 1H, d, J=15.3 Hz, CHH; 4.05 1H, d, J=15.3 Hz, CHH; 5.01 1H, dd, J=6.9 and 12.3 Hz, CH; 5.35 1H, br S, NH; 6.58 1H, dd, J=4.8 and 6.9 Hz, ArH; 7.17-7.29 5H, m, ArH; 7.93 1H, dd, J=2.1 and 4.8 Hz, ArH.

The product was used without further purification.

Method B. Dichlommethane Solution

A mixture of 2-amino-3-benzylpyrildine (11.6 g, 63.0 mmol) and bromoacetaldehyde dimethyl acetal (10.65 g, 63.0 mmol, 1.0 eq.) was dissolved in dichloromethane (100 ml. The stirred solution was cooled to 0° C. with an ice bath. Concentrated sulphuric acid (50 ml) was added in portions over ca. one minute to the cooled solution while stirring. A vigorous exothermic reaction took place. Stirring was continued for 3 hours while warming to room temperature. The mixture was poured on ice (ca. 500 ml). The resulting mixture was basified with concentrated ammonia (250 ml). Extraction was done with dichloromethane (3×200 ml). The combined organic layers were dried with $Na_2SO_4$. Evaporation under vacuum gave 10-bromomethyl-10,11-dihydro-5H-benzo[e]pyrido[2,3-b]azepine as a brown powder (15.3 g, 53.1 mmol) in 84% yield and 98% purity (LC-MS). The product was used without further purification.

EXAMPLE 3

The compounds obtained in example 2 (IIIb2, Q=Bromide) were optically resolved by diastereomeric salt resolution of the enantiomer mixture (10-bromomethyl-10,11-dihydro-5H-benzo[e]pyrido[2,3b]azepine).

A solution of S(+)-mandelic acid (7.0 g, 46.2 mmol) in EtOH (100 ml) was added to a warm solution of bromide (13.3 g, 46.2 mmol) in EtOH (400 ml). The mixture was heated to reflux and then slowly cooled to room temperature while stirring in the heating mantle. After 4 hours the suspension was filtered over a P2-glass filter to give a pale brown solid. The solid was washed with 2-propanol (10 ml) and isopropyl ether (25 ml) and then dried under vacuum to give 7.7 g salt (17.5 mmol; $M_{salt}$=440) in 38% yield with 59% d.e. (chiral HPLG). Recrystallization in EtOH (200 ml) gave 5.2 g salt with 74% d.e. Again recrystallization from EtOH (70 ml) gave 83% d.e. After two more recrystallizations the free base was liberated with aq. $Na_2CO_3$/dichloromethane to give bromide R(−)-10-bromomethyl-10,11-dihydro-5H-benzo[e]pyrido[2,3-b]azepine with 92% e.e.

The first filtrate from above was concentrated under vacuum to give 6.3 g salt (21.8 mmol). The free base was liberated and dissolved in EtOH (250 ml). R(−)-mandelic acid (0.8 eq., 2.66 g, 17.5 mmol was added. The mixture was heated to reflux and then cooled to room temperature overnight. The suspension was filtered over a glass filter. The salts were washed with EtOH (10 ml) and isopropyl ether (25 ml). Drying under vacuum gave 3.9 g salt (8.9 mmol) in 19% yield with 86% d.e. Recrystallization from EtOH (40 ml) gave after hot filtration 3.2 g salt with 92% d.e. After two more recrystallizations the salt was obtained with 97% d.e. Liberation of the free base gave bromide S(+)-1 bromomethyl-10,11-dihydro-5H-benzo[e]pyrido[2,3-b]azepine with 97% e.e.

Chiral HPLC analysis: column Chiralcel OJ (250×4.6 mm; 5 μm), mobile phase: n-heptane/2-PrOH/Et$_2$NH (60:40:0.2), flow: 1.0 ml/min, UV: 248 and 308 nm, sample: ~1 mg/ml in 2-propanol, injection: 10 μl, temp: 22° C. Enantiomers at 10.3 min (minor) and 24.9 min. (major R-isomer).

EXAMPLE 4

A methyl ester compound according to formula IIIb1 wherein Q=OMe (10,11-dihydro-5H-benzo[e]pyrrido[2,3-b] azepine-10-carboxylic acid methyl ester) was prepared as described below.

A mixture of 2-amino-3-benzylpyridine (18.3 g, 99.4 mmol; crude) and methyl 2,2-dimethoxyacetate (22 g, 21.6 mmol, 1.9 eq.) in a 250 ml round-bottomed flask was treated at room temperature with concentrated, sulphuric acid (50 ml) by quick addition while stirring. A vigorous exothermic reaction took place. After stirring for 30 minutes the dark mixture was poured on ice water (1000 ml). Concentrated ammonia (25% aq.; 250 ml) was added to basify the mixture. Extraction with dichloromethane (2×150 ml). The combined organic layers were dried with $Na_2SO_4$. Evaporation under vacuum gave 10,11-dihydro-5H-benzo[e]pyrido[2,3-b] azepine-10-carboxylic acid methyl ester as a yellow foam (18.5 g, 72.8 mmol) in 73% yield. An analytically pure sample can be obtained by chromatography on silica gel. $R_f$=0.3 (EtOAc/n-heptane=1:1).

Mass analysis: $M^{+1}$=255 major peak.

$^1$H-NMR (CDCl$_3$) δ (ppm) 3.84 3H, s, OCH$_3$; 3.86 1H, d, J=15.5 Hz, CHH; 4.11 1H, d, J=15.5 Hz, CHH; 5.51 1H, d, J=5.7 Hz; 5.87 1H, br s, NH, 6.52 1H, dd, J=5.1 and 7.2 Hz, ArH; 7.08 1H, m, ArH; 7.20-7.31 4H, m, ArH; 7.88 1H, dd, J=1.5 Hz and 4.8 Hz, ArH.

M.p. 130.6° C.

Chiral HPLC analysis: column Chiralpak AD-H (250×4.6 mm; 5 μm), mobile phase: n-heptane/EtOH/Et$_2$NH (50:50.0.2), flow: 0.5 ml/min, UV: 248 and 308 nm, sample: ~1 mg/ml in 2-propanol, injection: 10 μl, temp: 22° C. Enantiomers at 44.8 ((+)-isomer) and 68.5 min. ((−)-isomer).

The product was used without further purification.

EXAMPLE 5

The methyl ester compound obtained in example 4 (IIIb1, Q=OMe) was optically resolved by diastereomeric salt resolution.

A mixture of methyl ester (10,11-dihydro-5H-benzo[e]pyrido[2,3-b]azepine-10-carboxylic acid methyl ester) (2.14 g, 8.41 mmol) in EtOH (35 ml) and (−)-dibenzoyl-L-tartaric add (3.01 g, 8.41 mmol) was stirred at 70° C. until a clear solution was obtained. While cooling to room temperature salts precipitated. After 18 hours the precipitated salts were filtered over a glass filter. The solids were washed with EtOH (10 ml), isopropanol (10 ml) and isopropyl ether (25 ml). Drying under vacuum gave the diastereomeric salt (1.54 g, 2.52 mmol) in 30% yield with 80% d.e. The ee was determined as follows. Treatment of a sample of the salt with aq. $Na_2CO_3$ and extraction with $CH_2Cl_2$ gave after evaporation an oil. Chiral HPLC analysis showed that the sample had 80% ee of the (−)- isomer. Repeated recrystallization of the salt from EtOH gave (−) with >99% ee.

EXAMPLE 6

An ethyl ester compound according to formula IIIb1 wherein Q=OEt (10,11-dihydro-5H-benzo[e]pyrido[2,3-b]azepine-10-carboxylic acid ethyl ester) was prepared as described below.

A mixture of 2-amino-3-benzylpyridine (2.1 g, 11.4 mmol) and ethyl 2,2-diethoxyacetate (3.8 g, 21.6 mmol, 1.9 eq.) in a 250 ml round-bottomed flask was treated at room temperature with concentrated sulphuric acid (110) by quick addition while stirring. A vigorous exothermic reaction took place. After stirring for 30 minutes the dark mixture was poured on ice water (100 ml). Concentrated ammonia (25% aq.; 25 ml) was added to basify the mixture. Extraction with ethyl acetate (2×50 ml). The combined organic layers were dried with $Na_2SO_4$. Evaporation under vacuum gave 10,11-dihydro-5H-benzo[e]pyrido[2,3-b]azepine-10-carboxylic acid ethyl ester as a dark yellow oil (2.4 g, 8.9 mmol) in 79% c.y. An analytically pure sample can be obtained by chromatography on silica gel $R_f$=0.3 (EtOAc/n-heptane=1:1).

Mass analysis: $M^{+1}$=269 major peak.
$^1$H-NMR ($CDCl_3$) δ (ppm) 1.28 3H, d, J=7.2 Hz, $CH_3$; 3.80 1H, d, J=15.5 Hz, CHH; 4.18 1H, d, J=15.5 Hz, CHH; 4.32 2H, q, J=7.2 Hz, $OCH_2$; 5.54 1H, d, J=5.1 Hz; 5.86 1H, br d, J=5.1 Hz, NH; 6.50 1H, dd, J=4.8 and 7.2 Hz, ArH; 7.08 1H, m, ArH; 7.20-7.30 4H, m, ArH; 7.88 1H, dd, J=1.5 Hz and 4.8 Hz, ArH.

Chiral HPLC analysis: column Chiralcel OF (250×4.6 mm; 5 μm), mobile phase: n-heptane/2-PrOH/$Et_2NH$ (95:5:0.2), flow: 1.0 ml/min, UV: 248 and 310 nm, sample: ~1 mg/ml in 2-propanol, injection: 10 μl, temp: 22° C. Enantiomers at 75.3 ((4)-isomer and 83.6 min. ((−)-isomer).

The product was used without further purification.

EXAMPLE 7

The ethyl ester compound obtained in example 6 (IIIb1, Q=OEt) was optically resolved by diastereomeric salt resolution.

A warm solution of the ethyl ester (3.2 g, 11.94 mmol) in EtOH (50 ml) at 70° C. was treated with (−)-dibenzoyl-L-tartaric acid (4.27 g, 11.94 mmol). The mixture was stirred at 70° C. for 30 minutes. The resulting clear solution was stirred while cooling to room temperature. The precipitated salts were filtered over a glass filter. The solids were washed with EtOH (10 ml), isopropanol (10 ml) and isopropyl ether (25 ml). Drying under vacuum gave the diastereomeric salt (2.2 g, 3.51 mmol) in 29% c.y. with 88% d.e. The ee was determined as follows. Treatment of a sample of the salt with aq. $Na_2CO_3$ and extraction with $CH_2Cl_2$ gave after evaporation an oil. Chiral HPLC analysis showed that the sample had 88% ee of the (−)-enantiomer. Repeated recrystallization of the salt from EtOH gave (−)- with >99% ee. The absolute configuration of the (−)-isomer is not known.

Evaporation of the combined filtrates, basifying with aq. $Na_2CO$, and extraction with $CH_2Cl_2$ gave 2.2 g (8.2 mmol) of the opposite enantiomer (+)- (39% e.e.) with 69% recovery.

EXAMPLE 8

A carboxamide compound according to formula IIIb1 wherein Q NHMe (10,11-dihydro-5H-benzo[e]pyrido[2,3-b]azepine-10-N-methylcarboxamide) was prepared as described below using 2 different methods A and B Method A. from Methyl Ester Compound Obtained in Example 4:

Methylamine (250 ml 40% in water) was added to the crude methyl ester compound (22.5 g, 88.6 mmol) at room temperature. The mixture was heated to 65° C. on a water bath for 5 minutes. The obtained solution was stirred overnight while cooling to room temperature. The reaction mixture was heated to reflux for one hour and then evaporated under vacuum to dryness. Toluene (50 ml) was added and the mixture was evaporated to dryness. Acetone (50 ml) was added and the mixture was again evaporated to dryness to give the crude racemic carboxamide nearly quantitatively.

Mass analysis: $M^{+1}$=254 major peak
$^1$H-NMR ($CDCl_3$) δ (ppm) 2.88 3H, quasi d, N—$CH_3$; 3.49 1H, d, J=15.0 Hz, CHH; 4.15 1H, d, J=15 Hz, CHH; 4.92 1H, br 5, CH; 5.95 1H, br s, NH; 6.58 1H, dd, J=5.1 and 7.5 Hz, ArH; 6.96 1H, br 5, NH; 7.16-7.32 5H, m, ArH; 7.90 1H, dd, J=1.2 and 5.1 Hz, ArH.

The crude product was used without further purification.
Method B. From Ethyl Ester Compound Obtained in Example 6

A mixture of ethyl ester (500 mg, 1.87 mmol) and 40% aqueous methylamine (50 ml) was stirred at room temperature overnight to give complete conversion to the N-methylamide. Extraction was done with toluene (2×50 ml) and dichloromethane (2×50 ml). The combined organic extracts were dried with $Na_2SO_4$, Evaporation under vacuum gave pure amide in nearly quantitative yield according to $^1$H-NMR and mass analysis. $M^{+1}$=254 found

EXAMPLE 9

The carboxamide compound obtained in example 8 (IIIb1, Q=NHMe) was optically resolved by diastereomeric salt resolution.

A mixture of the racemic carboxamide compound (19.2 g, 75.9 mmol) and S(+)-mandelic acid (11.54 g, 1.0 eq.) was mixed with ethanol (100 ml). The suspension was shortly heated to 65° C. to give a clear solution. The warm solution was stirred while cooling to room temperature. After 24 hours the salts were filtered over a glass filter under suction. The finely divided powder was washed with ethanol (10 ml) and then washed with isopropyl ether (2×40 ml). The residual solid was dried under vacuum to give the S(+)-mandelic acid salt (9.4 g, 23.2 mmol) as an off-white solid in 31% yield with 74% d.e., according to chiral HPLC of the liberated S(+)-carboxamide. The salt was recrystallized from ethanol to give 6.8 g salt with 86% d.e.

The combined filtrates were basified with aqueous $Na_2CO_3$ and the corresponding R(−)-isomer was extracted with dichloromethane. The organic layer was dried with $Na_2SO_4$. Evaporation under vacuum gave R(−)-enantiomer (6.4 g, 25.3 mmol) with 44% e.e. Then, R(−)-mandelic acid (2.88 g, 18.95, mmol, 0.72 eq,) and ethanol (25 ml) were added. The mixture was warmed to give a clear solution. Upon stirring while cooling to room temperature precipitation of the R(−)-mandelic acid salt of R(−)-enantiomer took place. The salt was filtered over a glass filter and washed with ethanol (5 ml) and isopropyl ether (2×25 ml). After drying under vacuum 4.0 g (9.88 mmol) of the R(−)-mandelic acid salt of R(−)-enantiomer was obtained in 39% yield with 98% d.e. Treatment of the salt with aqueous $Na_2CO_3$ and extraction with $CH_2Cl_2$ gave pure R(−)-amide.

EXAMPLE 10

An extended compound hydroxyethyl-carboxamide compound (according to formula IIIb1 with Q=HOC$_2$H$_4$NMe-) (10,11-dihydro-5H-benzo[e]pyrrido[2,3-b]azepine-10-N-(2-hydroxyethyl)-carboxamide) was prepared as described below using 2 different methods A and B.
Method A. From Methyl Ester Compound Obtained in Example 4:
2-(N-methyl)-aminoethanol (25 g, 330 mmol) was added to a preheated solution of 10,11-dihydro-5H-benzo[e]pyrido[2,3-b]azepine-10-carboxylic acid methyl ester (27.5 g, 108.3 mmol) in THF (100 ml) at 75° C. while stirring. After 30 minutes ca. 15% conversion was observed by LC-MS. The reaction mixture was stirred for 3 days at room temperature. Concentration under vacuum (at 95° C.) gave a brown solid. Dichloromethane (200 ml) was added and after stirring for 5 minutes the mixture was filtered over a glass filter. The solid residue was washed with ethyl acetate (300 ml) and acetone (50 fry). Drying under vacuum gave the amide as an off-white solid (18.4 g, 61.95 mmol) in 57% yield. From the combined filtrates a second crop of amide was isolated by filtration and drying.
Mass analysis. $M^{+1}$=298 major peak.
$^1$H-NMR (dmso-d6) δ (ppm) (appears as a mixture of amide rotamers) 2.80 1.8H, s, N—CH$_3$; 3.05 1.2H, s, N—CH$_3$; 3.16-3.70 6H, m, 4.71 1H d, J=15 Hz, CHH; 4.83 1H, d, J=15 Hz, CHH; 5.96 1H, dd; J=5.1 and 9.9 Hz; 6.23 1H, dd, J=5.1 and 10.2 Hz; 6.46 1H, dd, J=4.8 and 6.9 Hz, ArH; 6.88 0.34H, m, NH; 7.00 0.66H, m, NH; 7.21-7.31 5H, m, ArH; 7.75 1H, d, J=51 Hz, ArH.
Method B. From Ethyl Ester Compound Obtained in Example 6:
A mixture of 2-(N-methyl)-aminoethanol (10 g, 133.2 mmol) and 10,11-dihydro-5H-benzo[e]pyrido[2,3-b]azepine-10-carboxylic acid ethyl ester (2.0 g, 7.46 mmol) was heated for 15 minutes at 70° C. while stirring. The resulting mixture was stirred for 5 days at room temperature. The mixture was concentrated under vacuum (at 90° C.) to give the amide as a brown solid in nearly quantitative yield.
Mass analysis; $M^{+1}$=298 major peak. The product was used without further purification.

EXAMPLE 11

A hydroxyethylmethylamide compound (according to formula IIIb2 with Q=HOC$_2$H$_4$NMe-) according to formula IIIb2 (10,11-dihydro-5H-benzo[e]pyrido[2,3-b]azepine-10-yl-(2-hydroxyethyl)-methylamine), was prepared as described below using 2 different methods A and B
Method A. From the Bromide Compound Obtained in Example 2 and N-methylaminoethanol
A solution of 10-bromomethyl-10,11-dihydro-5H-benzo[e]pyrido[2,3-b]azepine (13.4 g, 46.5 mmol) 2-(methylamino)ethanol (31 g, 413.3 mmol; 8.9 eq.) and $K_2CO_3$ (26 g, 188.4 mmol; 4 eq.) was heated to reflux in acetonitrile (50 ml) for 15 minutes and then stirred over the weekend (3 days) while cooling to room temperature in the shut-off heating mantle. The reaction mixture was concentration under vacuum. Water was added and the crude product was extracted with dichloromethane (2×25 ml). The dichloromethane solution was dried, with $Na_2SO_4$, filtered and concentrated to give the crude hydroxyethylamine, which could be used directly in the following step. A sample of 4 g crude material was purified by automated ISCO chromatography and afforded 510 mg (1.77 mmol) analytically pure product.
$^1$H-NMR (CDCl$_3$) δ (ppm) 2.39 3H, s, CH$_3$; 2.58-2.86 3H, m; 3.12 1H, t, J=11.7 Hz; 3.52 1H, d, J=15.0 Hz, CHH; 3.61-3.75 3H, m; 4.64 1H d, J=15.0 Hz, CHH; 5.17 1H, dd; J=3.9 and 10.8 Hz; 6.01 1H, br s, NH; 6.45 1H, m, ArH; 7.12-7.30 5H, m; ArH; 7.77 1H, d, J=4.8 Hz.
Method B. From the Methyl Amine Compound Obtained in Example 2 and Bromoethanol
Potassium carbonate (14.6 g, 105.8 mmol, 2 eq.) was added to a mixture of amine 10,11-dihydro-5H-benzo[e]pyrido[2,3-b]azepin-10-ylmethyl)-methyl-amine (13.7 g, 57.3 mmol) and bromoethanol (1.0 eq., 7.16 g) in DMF (50 ml). The mixture was heated to reflux for 5 hours. Evaporation of the solvent under vacuum, addition of dichloromethane and washing with water gave after drying of the organic layer with $Na_2SO_4$ and concentration under vacuum the product in nearly quantitative yield.

EXAMPLE 12

Mirtazapine was prepared from 10,11-dihydro-5H-benzo[e]pyrido[2,3-b]azepine-10-yl-(2-hydroxyethyl)-methylamine obtained in Example 11.

10,11-dihydro-5H-benzo[e]pyrido[2,3-b]azepine-10-yl-(2-chloroethyl)-methylamine

Thionyl chloride (2 ml) was added to a solution of 10,11-dihydro-5H-benzo[e]pyrido[2,3-b]azepine-10-yl-(2-hydroxyethyl)-methylamine in dichloromethane (15 ml) at room temperature to replace the hydroxy group with a stronger leaving group. After stirring for one hour the reaction mixture was concentrated under vacuum to give the crude chloride compound as a brown oil. Mass analysis. $M^{+1}$=302, 304 (Cl-isotope).
Mirtazapine
The crude 10,11-dihydro-5H-benzo[e]pyrido[2,3-b]azepine-10-yl-(2-chloroethyl)-methylamine obtained (some starting material present) was dissolved in DMF (10 ml). $K_2CO_3$ (800 mg) and KI (500 mg) were added. The mixture was refluxed for 4 hours. Dilution with water (100 ml) and extraction with dichloromethane (2×100 ml) gave after drying with $Na_2SO_4$ and evaporation crude racemic mirtazapine as an oil.
$^1$H-NMR (CDOC) δ (ppm) 2.32 1H, dd, J=3.3 and 10.8 Hz, H-3; 2.37 3H, s, N—CH$_3$; 2.51 1H, t, J=10.2 Hz, H-1; 2.86 1H, m, H-1; 2.96 1H, m, H-3; 3.42 1H, d, J=13.2 Hz, H-10; 3.50 1H, m, HA; 3.69 1H, m; H-4; 4.35 1H, dd, J=2.4 and 9.9 Hz, H-14b; 4.52 1H, d, J=13.5 Hz, H-10; 6.72 1H, dd, J=4.8 and 7.2 Hz, H-8; 7.14 4H, m, ArH; 7.30 1H, m, H-9; 8.15 1H, dd, J=1.8 and 5.1 Hz, H-7.

EXAMPLE 13

Mirtazapine was prepared from 10,11-dihydro-5H-benzo[e]pyrido[2,3-b]azepine-10-N-(2-hydroxyethyl)-carboxamide obtained in example 10.

10,11-dihydro-5H-benzo[e]pyrido[2,3-b]azepin-10N-(2-chloroethyl-carboxamide

Thionyl chloride (13.5 ml) was added to a suspension of 10,11-dihydro-5H-benzo[e]pyrido[2,3-b]azepine-10-N-(2-hydroxyethyl)-carboxamide (18.6 g, 61.95 mmol) in chloroform (100 ml) at room temperature. The mixture was stirred overnight at room temperature. Evaporation under vacuum gave an oily product. The residue was coevaporated with toluene (50 ml) under vacuum to give the crude chloride as a beige solid in quantitative yield. Mass analysis: $M^{+1}$=316,318 (Cl-isotope).

The chloride was used without further purification.

3,4,10,14b-tetrahydro-2-methyl-pyrazino[2,1-a]pyrido[2,3-c][2]benzazepin-1(2H)-one A mixture of crude 10,11-hydro-5H-benzo[e]pyrido[2,3-b]azepine-10-N-(2-chloroethyl)-carboxamide (2.4 g, 7.46 mmol), $K_2CO_3$ (3.5 g, 25.4 mmol) and KI (2.7 g, 16.3 mmol) in DMF (100 ml) was heated to reflux while stirring. After 3 hours the heating was stopped and the mixture was stirred overnight while cooling to room temperature. The mixture was evaporated under vacuum at 85° C. Water (50 ml) was added and the mixture was extracted with a mixture of dichloromethane/methanol (95:5, 100 ml). The organic extract was concentrated under vacuum. The obtained brown oil was dissolved in acetone (10 ml). Upon addition of t-butyl methyl ether (50 ml) a beige precipitate was formed which was filtered over a glass filter under suction. Drying under vacuum gave 0.28 g of the title compound (13% yield) as a white solid. The remaining filtrate was evaporated under vacuum and the residue was purified by chromatography on silica gel, eluting with dichloromethane/methanol=9.1 ($R_f$=0.1) to give another crop of the title compound as a white solid.

Mass analysis: $M^{+1}$=280.

$^1$H-NMR (CDCl$_3$) δ (ppm) 3.19 3H, s, N—CH$_3$; 3:30-3.44 2H, m; 3.49 1H, d, J=16.2 Hz, CHH; 3.71 1H, m; 4.42 1H, m; 4.83 1H, d, J=16.2 Hz, CHH; 5.90 1H, s; 6.63 µl, dd, J=5.1 and 7.5 Hz, ArH; 7.09 1H, m, ArH; 7.23 3H, m, ArH; 7.33 1H, d, J=6.9 Hz, ArH; 8.0 1H, dd, J=0.9 and 5.1 Hz, ArH.

Mirtazapine 3,4,10,14b-tetrahydro-2-methyl-pyrazino[2,1-a]pyrido[2,3-c][2]benzazepin-1(2H)-one (200 mg, 0.72 mmol) was dissolved in dichloromethane (40 ml). BF$_3$.OEt$_2$ (0.5 ml) was added while cooling to 0° C. with an ice-water bath under stirring. A yellow precipitate 35 was formed. After 15 minutes BH$_3$.SMe$_2$ (10 ml 2.0 M in THF) was added in one portion. The mixture was stirred overnight while warming to room temperature, Water was added, followed by addition of an aqueous Na$_2$CO$_3$ solution. The water phase was extracted with dichloromethane (3×25 ml) and the organic extract was dried with Na$_2$SO$_4$. Evaporation under vacuum gave crude mirtazapine as a yellow solid (246 mg). Purification by chromatography gave pure mirtazapine (105 mg, 0-4 mmol) in 55% yield.

Mass analysis: $M^{+1}$=26

EXAMPLE 14

(R)-mirtazapine is prepared from R(-)-10,11-dihydro-5H-benzo[e]pyrido[2,3-b]azepine-10-N-methylcarboxamide obtained in example 9.

R-10,11-dihydro-5H-benzo[e]pyrido[2,3-b]azepin-O-ylmethyl)-methyl-amine

Method A. LiAlH$_4$ Reduction of Amide

The R(-)-mandelic acid salt of R(-)-10,11-dihydro-5H-benzo[e]pyrido[2,3-b]azepine-10-N-methylcarboxamide (2.75 g, 6.79 mmol, 98% d.e.) was mixed with saturated aqueous Na$_2$CO$_3$ (25 ml) and dichloromethane (50 ml). After vigorous mixing the dichloromethane layer was separated, dried with Na$_2$SO$_4$ and concentrated under vacuum to give the free base of R(-)-10,11-dihydro-5H-benzo[e]pyrido[2,3-b]azepine-10-N-methylcarboxamide as a foam. THF (25 ml) was added and a clear solution was obtained. This THF solution was added dropwise to a stirred suspension of LiAlH$_4$ (516 mg, 13.58 mmol; 2 eq.) in dry THF (25 ml) under inert nitrogen atmosphere. After 90 minutes stirring at room temperature no reaction had taken place and the mixture was heated to reflux for 2 hours while stirring. The reaction mixture was quenched by careful addition of water (10 ml) and a concentrated aqueous potassium sodium tartrate solution (50 ml). The mixture was extracted with dichloromethane. The organic layer was dried with Na$_2$SO$_4$ and concentrated under vacuum to give an oil (1.3 g), containing of 30% starting material and 70% R-10,11-dihydro-5H-benzo[e]pyrido[2,3-b]azepin-1-ylmethyl)-methyl-amine, according to LC-MS. Chiral HPLC analysis on R-4-b 87% ee. Enantiomers at 13.8 (major) and 18.0 min. (minor).

Method B. BH$_3$.SMe$_2$ Reduction of Amide

The R(-)-mandelic acid salt of amide R(-)-10,11-dihydro-5H-benzo[e]pyrido[2,3-b]azepine-10-N-methylcarboxamide (1.0 g, 2.47 mmol; 98% d.e.) was mixed with saturated aqueous Na$_2$CO$_3$ (20 ml) and dichloromethane (50 ml). After vigorous mixing the dichloromethane layer was separated. The aqueous layer was extracted with dichloromethane (25 ml). The combined organic fractions were dried with Na$_2$SO$_4$ and concentrated under vacuum to give the free amide R(-)-10,11-dihydro-5H-benzo[e]pyrido[2,3-b]azepine-10-N-methylcarboxamide as a foam. The amide was mixed with dichloromethane (25 ml) and BF$_3$.OEt$_2$ (0.5 ml, 2.35 mmol) was added while stirring at 0° C. After 5 minutes BH$_3$.SMe$_2$ (6.0 ml, 2.0 M in THF; 12.0 mmol) was added. After 18 hours at room temperature very low conversion was observed and again BF$_3$.OEt$_2$ (3 ml, 14.1 mmol) was added under vigorous gas evolution. After 20 hours the mixture was poured in ice water (100 ml), Sat, aq. Na$_2$CO$_3$ (100 ml) was added and the mixture was extracted with dichloromethane (2×100 ml). The organic extracts were dried with Na$_2$SO$_4$ and concentrated under vacuum to give the crude product (443 mg, 1.85 mmol) in 75% yield as a yellow oil. Purification by chromatography on silica gel gave the pure product 4b (266 mg, 1.11 mmol) in 45% c.y.

Chiral HPLC analysis on R-4b: 98% e.e.

R-10,11-dihydro-5H-benzo[e]pyrido[2,3-b]azepine-10-yl-(2-hydroxyethyl)-methylamine Crude R-10,11-dihydro-5H-benzo[e]pyrido[2,3-b]azepin-10-ylmethyl)-methyl-amine was dissolved in DMF (25 ml) and 2-bromoethanol (0.85 g, 6.8 mmol), K$_2$CO$_3$ (3.9 g, 28.3 mmol) and KI (2.0 g, 12.0 mmol) were added. The mixture was heated overnight while stirring. The mixture was filtered over a glass filter and the filtrate was concentrated under vacuum to give the crude alcohol. Purification by chromatography on silica gel, eluting with CH$_2$Cl$_{21}$MeOH mixtures (100.0-90:10), gave R-10,11-dihydro-5H-benzo[e]pyrido[2,3-b]azepine-10-yl-(2-hydroxyethyl)-methylamine (1.4 g, 4.95 mmol) in 73% yield.

R-mirtazapine

R-10,11-dihydro-5H-benzo[e]pyrido[2,3-b]azepine-10-yl-(2-hydroxyethyl)-methylamine was dissolved in dichloromethane (50 ml). Thionyl chloride (3 ml) was added at room temperature. After stirring for 15 minutes the mixture was evaporated under vacuum. Toluene (50 ml) was added and the mixture was again concentrated under vacuum. The resulting clear brown oil (the intermediate chloride) was dissolved in DMF (50 ml). K$_2$CO$_3$ (6.0 g, 43.5 mmol) and KI (3.0 g, 18.1 mmol) were added and the resulting mixture was heated to reflux for 90 minutes, stirred overnight at room temperature and heated to reflux for one hour. The mixture was evaporated under vacuum at 85° C. with a rotary evaporator. CH$_2$CO$_2$ (50 ml) was added to the residue and the resulting slurry was filtered over a glass filter. Evaporation under vacuum gave crude R(−)-mirtazapine as an oil. Purification by chromatography on silica gel, eluting with CH$_2$Cl$_2$/MeOH 9.1 (TLC, R$_f$=0.45; staining with 12 vapor), gave R(−)-mirtazapine (1.0 g, 3.7 mmol) in 78% yield. Chiral HPLC analysis: 98% e.e. R(−)-mirtazapine.

EXAMPLE 15

S(+)-mirtazapine is prepared from S(+)-10-bromomethyl-10,11-dihydro-5H-benzo[e]pyrido[2,3-b]azepine as obtained in example 3.

S-10,11-dihydro-5H-benzo[e]pyrido[2,3-b]azepine-10-yl-2-hydroxyethyl)-methylamine S(+)-10-bromomethyl-10,11-dihydro-5H-benzo[e]pyrido [2,3-b]azepine (1 g, 3.53 mmol; 97% e.e.), 2-(methylamino) ethanol (1 g, 13.3 mmol; 3.8 eq.) and K$_2$CO$_3$ (1 g, 7.3 mmol; 2 eq.) was heated to reflux in acetonitrile (50 ml) overnight. After one hour MS-analysis showed the formation of S-7 (M$^{+1}$=284 found). The reaction mixture was concentrated under vacuum. Water was added and the crude product S-7 was extracted with dichloromethane (2×25 ml). The dichloromethane solution was dried with Na$_2$SO$_4$ and filtered. Purification by chromatography gave S-10,11-dihydro-5H-benzo [e]pyrido[2,3-b]azepine-10-yl-(2-hydroxyethyl)-methylamine 599 mg, 2.21 mmol) in 60% yield.

S-mirtazapine

Thionyl chloride (2 ml) was added to a dichloromethane solution (20 ml) of S-10,11-dihydro-5H-benzo[e]pyrido[2,3-b]azepine-10-yl-(2-hydroxyethyl)-methylamine at room temperature. After stirring for one hour, the reaction mixture was concentrated under vacuum to give the crude intermediate chloride. The crude chloride was dissolved in acetonitrile (100 ml). K$_2$CO$_3$ (1.5 g, 10.9 mmol) and KI (1 g, 6.0 mmol) were added. The mixture was refluxed overnight while stirring. Evaporation under vacuum. Water (50 ml) was added. Extraction with dichloromethane (3×50 ml), drying with Na$_2$SO$_4$ and concentration under vacuum gave an oil, Mass analysis. M$^{+1}$=266 (mirtazapine) found. An analytically pure sample of S(+)-mirtazapine (439 mg, 1.65 mmol; 75% yield) was obtained by chromatography on silica gel. Chiral HPLC analysis (Chiralcel OF column): 97% e.e. S(+)-mirtazapine.

The invention claimed is:

1. A method for the preparation of a cyclic compound according to Formula IIIa, comprising reacting 2-amino-3-benzylpyridine according to Formula Ib and a compound according to Formula II,

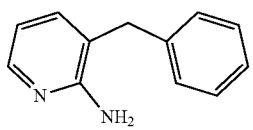

Formula Ib

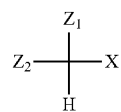

Formula II

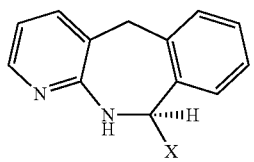

Formula IIIa wherein,
Z$_1$ and Z$_2$ are leaving groups, or together form oxygen creating the corresponding aldehyde;
X is a hydrocarbon having a carbon atom attached to the central carbon atom of formula II, comprising a reactive functional group and optionally a nitrogen atom, chosen in view of one or more subsequent reaction steps starting from the compound according to Formula IIIa to a ring closure to form mirtazapine; or X is —CO-Q or —CH$_2$-Q, wherein Q is a hydrogen, or halogen, or a hydrocarbon substituent optionally comprising a nitrogen atom, or Q is —NHR or —OR wherein R is hydrogen or a hydrocarbon substituent.

2. The method according to claim 1 wherein the leaving group Z$_1$ and Z$_2$ in Formula II each independently are hydroxide, alkoxide, chloride, bromide, iodide, triflate, mesylate, tosylate or besylate.

3. The method according to claim 1 wherein in Formula II Z$_1$ and Z$_2$ are OR$_6$ and OR$_7$ respectively wherein R$_6$ and R$_7$ are hydrocarbon or hydrogen as indicated in Formula IIa, or
Z$_1$ and Z$_2$ are together oxygen creating the corresponding aldehyde as indicated in Formula IIb

Formula IIa

Formula IIb

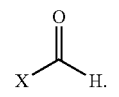

4. The method according to claim 1 for the preparation of the compound of Formula IIIb1 in enantiomeric excess FORMULA IIIb1

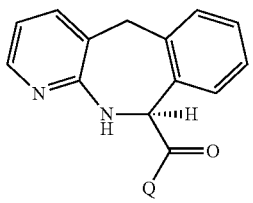

further comprising the steps:
1: subjecting a racemic mixture of said compound to an optical resolution step,
2: separating the desired enantiomer,
3: racemising the undesired enantiomer and
4: recycling the racemised undesired enantiomer to the optical resolution step 1.

5. The method according to claim 4, wherein the compound of Formula IIIb1 is further reduced to a compound of Formula IIIb2

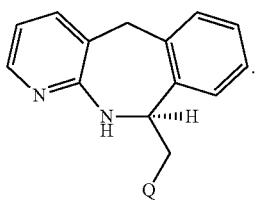

Formula IIIb2

6. The method according to claim 5, wherein Q is —NMeC$_2$H$_4$L, wherein L is a group reactive with the ring amine.

7. The method according to claim 1, wherein X is —CO-Q or —CH$_2$-Q, the reactive group in Q is reacted with an extender compound according to the Formula L-CH$_2$—CH$_2$—NMe-A, wherein L is a group reactive with the ring amine and A is a group reactive with Q.

8. The method according to claim 7, wherein Q is a halogen, —NHR or —OR wherein R is hydrogen or a hydrocarbon substituent.

9. A compound according to Formula IIIb in racemic, enantiomeric excess or enantiomeric pure R or S form,

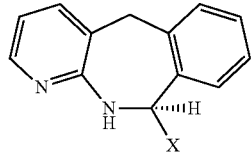

Formula IIIb wherein X is a hydrocarbon having a carbon atom attached to the central carbon atom of formula II, comprising a reactive functional group and optionally a nitrogen atom, chosen in view of one or more subsequent reaction steps starting from the compound according to Formula IIIa to a ring closure to form mirtazapine; or X is —CO-Q or —CH$_2$-Q, wherein Q is a hydrogen, or halogen, or a hydrocarbon substituent optionally comprising a nitrogen atom, or Q is —NHR or —OR wherein R is hydrogen or a hydrocarbon substituent.

10. A compound according to Formula IVb1 or IVb2 in enantiomeric pure form,

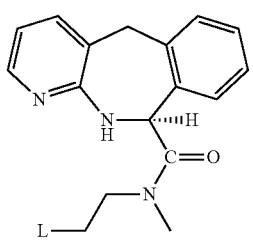

Formula IVb1

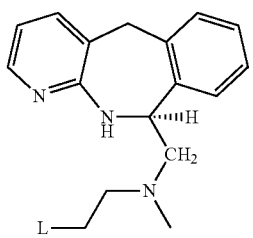

Formula IVb2 wherein L is a group reactive with the ring amine.

* * * * *